(12) United States Patent
Feygin

(10) Patent No.: US 6,524,531 B1
(45) Date of Patent: Feb. 25, 2003

(54) HAND-HELD DISPENSER/ASPIRATOR

(75) Inventor: Ilya Feygin, Mountainside, NJ (US)

(73) Assignee: Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 09/395,399

(22) Filed: Sep. 14, 1999

(51) Int. Cl.[7] .............................. B01L 3/00; B01L 3/02; B01L 11/00; G01N 1/10; G01N 1/04; G01N 1/12

(52) U.S. Cl. .................. 422/100; 422/99; 422/102; 422/103; 436/180; 73/863.32; 73/864; 73/864.01; 73/863.72; 73/863.71; 73/864.91

(58) Field of Search ..................... 422/99, 100, 102, 422/103; 436/180; 73/864.01, 863.32, 864, 863.71, 863.72

(56) References Cited

U.S. PATENT DOCUMENTS

| | | | | |
|---|---|---|---|---|
| 3,012,863 A | * | 12/1961 | Feichtmeir | 422/100 |
| 3,192,969 A | * | 7/1965 | Baruch et al. | 422/100 |
| 3,476,518 A | * | 11/1969 | Junger | 422/100 |
| 3,492,876 A | * | 2/1970 | Bull et al. | 422/100 |
| 3,805,998 A | * | 4/1974 | Croslin | 222/32 |
| 4,010,648 A | * | 3/1977 | Harris, Sr. et al. | 73/423 R |
| 4,011,685 A | * | 3/1977 | Boyd et al. | 47/57.5 |
| 4,567,780 A | * | 2/1986 | Oppenlander et al. | 73/864.16 |
| 5,053,100 A | * | 10/1991 | Hayes et al. | 156/294 |
| 5,364,595 A | * | 11/1994 | Smith | 422/100 |
| 5,874,296 A | * | 2/1999 | Kang | 435/283.1 |
| 5,976,468 A | * | 11/1999 | Godec et al. | 422/100 |
| 6,007,776 A | * | 12/1999 | Matsumoto | 422/68.1 |
| 6,077,713 A | * | 6/2000 | Dunfee et al. | 436/180 |
| 6,244,119 B1 | * | 6/2001 | Theran | 73/864.17 |
| 2001/0016177 A1 | * | 8/2001 | Pelc et al. | 422/100 |

* cited by examiner

Primary Examiner—Jill Warden
Assistant Examiner—Brian R Gordon
(74) Attorney, Agent, or Firm—DeMont & Breyer, LLC

(57) ABSTRACT

A hand-held, single-channel dispenser/aspirator is disclosed. The present dispenser/aspirator comprises a body portion for gripping the dispenser and a head portion. In some embodiments, the head portion includes a valve, a liquid conduit and a removable liquid reservoir. The liquid conduit places the liquid reservoir and the dispensing valve in fluid communication. A gas conduit received by the body portion of the dispenser is operable to pressurize the fluid reservoir, or draw a partial vacuum therein. Controls located on the body portion operate the dispenser. The liquid reservoir is advantageously disposed near the valve, so that a relatively short length of liquid conduit is required to operatively connect the reservoir and the dispensing valve, thereby improving the accuracy of the dispensing operation.

14 Claims, 2 Drawing Sheets

HAND-HELD DISPENSER/ASPIRATOR

FIELD OF THE INVENTION

The present invention relates to hand-held liquid dispensers. More particularly, the present invention relates to a hand-held liquid dispenser/aspirator capable of dispensing/aspirating micro-liter volumes of liquid.

BACKGROUND OF THE INVENTION

In research and development settings, there are applications that require the transfer of a micro-volume amount of a single sample of reagent. Such a reagent, for example, might be withdrawn from a reservoir and delivered to a receiver, such as a well in a multi-well microtitre plate. It is usually important to perform such a transfer without cross-contamination such as may occur, for example, if a first reagent is already present in the well before a second reagent is transferred thereto.

To substantially eliminate the incidence of cross-contamination, a "non-touch-off" method of fluid delivery is advantageously used. In such a method, there is no contact between a droplet being dispensed and the receiver (or fluid or other material in the receiver) until the droplet completely disengages from the tip of the dispenser. Non-touch-off transfer requires supplying kinetic energy to a droplet in an amount sufficient to overcome the surface tension of the dispensing tip and to dispense the droplet with sufficient momentum that it can be accurately and reliably directed to a desired destination.

Sophisticated table-top multi-channel dispensers have been developed for simultaneously dispensing micro volumes of liquid via non touch-off methods into a plurality of regularly spaced receivers. But relatively few "single channel" (e.g., one dispensing operation at a time) hand-held dispensers are available. And those that are available are relatively simple and inaccurate "syringe-" or "pipetter-" type dispensers. Such pipetter-type dispensers are typically incapable of dispensing micro volumes of fluid.

Thus, there remains a need for an improved hand-held single channel non-touch-off dispenser.

SUMMARY OF THE INVENTION

In accordance with some embodiments of the present invention, a hand-held, single-channel dispenser is disclosed.

The present dispenser comprises a body portion for gripping the dispenser and a head portion. In some embodiments, the head portion comprises a dispensing valve, a liquid conduit and a liquid reservoir. The liquid conduit places the liquid reservoir and the dispensing valve in fluid communication. A gas conduit received by the body portion of the dispenser is operable to pressure the liquid reservoir, or draw a partial vacuum therein. Controls located on the body portion operate the dispenser.

In accordance with the illustrated embodiments of the present invention, the liquid reservoir is advantageously disposed near the dispensing valve. As a result, a relatively short length of liquid conduit is required to operatively connect the reservoir and the dispensing valve, which improves the accuracy of the dispensing operation.

In some embodiments, the liquid reservoir advantageously comprises the container portion of a standard "screw-top" vial. The lid of the vial is mounted to the head portion of the dispenser. To ready the dispenser for use, the container portion is threaded into the lid. For dispensing operations, liquid is added to the container portion before it engages the lid. Alternatively, the container can be engaged to the lid empty, and, via the application of negative pressure, a liquid of choice can be aspirated into the container. Fittings are disposed through the lid so that the conduit and gas conduit can be introduced into the reservoir.

These and other features of the present invention are described in detail later in this Specification in the Detailed Description with reference to the attached Figures.

DETAILED DESCRIPTION

Figure 1:
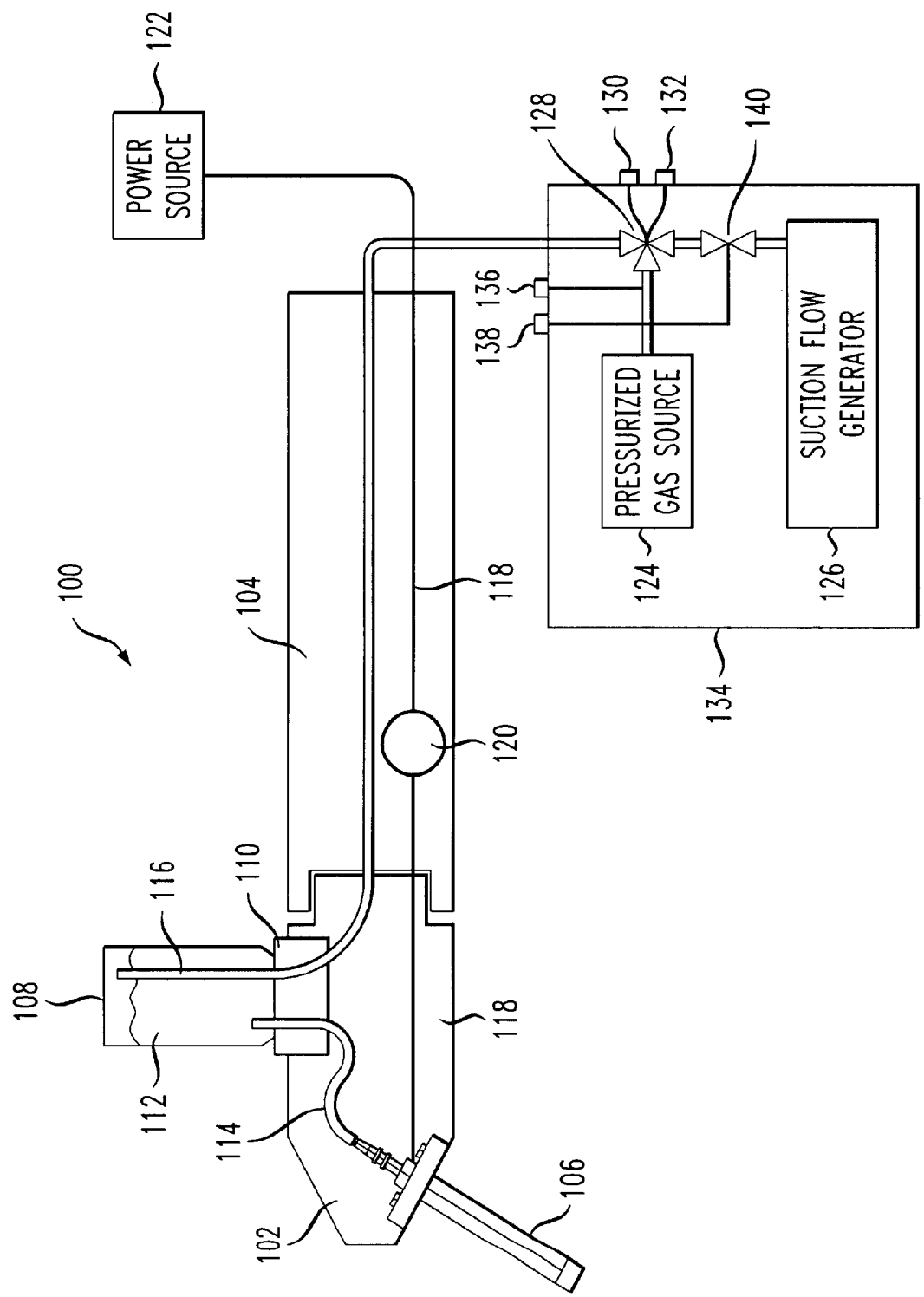
FIG. 1 depicts a hand-held single-channel dispenser/aspirator in accordance with an illustrated embodiment of the present invention.

FIG. 1 depicts illustrative hand-held liquid dispenser/aspirator 100 in accordance with an illustrated embodiment of the present invention. Dispenser/aspirator 100, hereinafter referred to as simply a "dispenser," comprises a head portion 102 detachably engaged to a body portion 104. In the illustrated embodiment, head portion 102 is smaller than body portion 104.

Head portion 102 includes dispensing valve 106 and liquid reservoir 108. Liquid conduit 114 places reservoir 108 in fluid communication with dispensing valve 106. As used herein, the phrase "fluid communication," indicates that fluid (i.e., liquid and/or gas) can flow directly between two regions (i.e., the two regions that are described to be in fluid communication). It should be understood even though valve 106 is referred to as a "dispensing" valve, it is also operable to aspirate liquid.

In embodiments wherein the present hand-held dispenser is intended to dispense micro-liters or less of liquid, the dispensing valve (i.e., valve 106) will be a "micro" valve, such as is used for print heads in ink-jet printers. Such micro-valves are capable of dispensing micro-volumes of liquid in the range of about 20 nano-liters to several micro-liters. Such micro-valves are currently available, such as from The Lee Company of Essex, Conn.

It is advantageous for liquid reservoir 108 to be readily removable from the dispenser. Such a configuration facilitates exchanging reservoirs, as desired. In particular, after a first reservoir dispenses its charge of liquid, it may be desirable to disengage it from the dispenser and engage a second reservoir containing a different liquid thereto. One example of a configuration by which reservoir 108 can be readily removed from the dispenser is described below.

In the illustrated embodiment, liquid reservoir 108 is realized as an ordinary screw-top vial. Lid 110 from such a vial is attached to head portion 102 of the dispenser. In use, the container portion of the vial is threaded into lid 110. For dispensing operations, an appropriate liquid 112 is first added to the container portion. It will be appreciated that when liquid 112 is present in the container, the dispenser should be inverted from the orientation depicted in FIG. 1 to thread the container to the lid.

Body portion 104 of illustrative dispenser 100 provides a means for a user to grip the dispenser for use. Power source 122, which supplies power for actuating dispensing valve 106, is electrically connected to dispensing valve 106 via lead 118 through button 120. Button 120, which is actuated by a user's finger, sends a signal to power source 122, which responds by sending a voltage pulse of preset length that defines the opening time of dispensing valve 106. In an aspirating mode (described below), power source 122 sends a group of pulses to dispensing valve 106 so that it remains open.

The present dispenser further comprises pressurization means by which reservoir 108 and liquid conduit 114 are pressurized. The present dispenser also advantageously comprises suction-flow means by which a partial vacuum is drawn through reservoir 108 and liquid conduit 114. Such suction flow allows the "dispenser" to aspirate (suck in) liquid. An illustrative arrangement for placing reservoir 108 and liquid conduit 114 under elevated pressure, or, alternatively, under partial vacuum, is now described.

In the illustrated embodiment, pressurization means comprises gas conduit 116 and a pressurized gas source 124. A first end of gas conduit 116 terminates in reservoir 108, and a second end of gas conduit 116 is placed in fluid communication with pressurized gas source 124 through operation of a mode selector, embodied as three-way valve 128 and switch 130.

When gas conduit 116 is connected to the pressurization means, reservoir 108 and liquid conduit 114 are pressurized. Such pressure imparts kinetic energy to liquid 112 when dispensing valve 106 opens, and a volume of fluid 112 is dispensed.

Similarly, in the illustrated embodiment, suction-flow generating means comprises gas conduit 116 and a suction flow generator 126. The suction flow generator can be, for example, a pump, jet ejector or the like. A first end of gas conduit 116 terminates in reservoir 108, and a second end of gas conduit 116 is placed in fluid communication with suction flow generator 126 through operation of a mode selector, embodied as a three-way valve 128 and switch 132.

When gas conduit 116 is connected to suction-flow generator 126, a suction flow (i.e., partial vacuum) is developed in reservoir 108 and liquid conduit 114. And, when dispensing valve 106 opens, a suction flow is generated therethrough so that any liquid in contact with the valve is aspirated into reservoir 108.

In the illustrated embodiment, pressurized gas source 124 and suction-flow generator 126 are figuratively depicted as being co-located in a single "box" 134. This illustration is meant to indicate that the mode selector for selecting dispensing or aspirating operation can be accessed via a single control box. Additionally, pressure control means, such as regulator (which is simply illustrated as switch 136 for clarity of illustration) are advantageously accessed via box 134. Also, means for controlling suction flow, such as controller 138 that is operatively connected to valve 140, are accessed via box 134.

Figure 2:
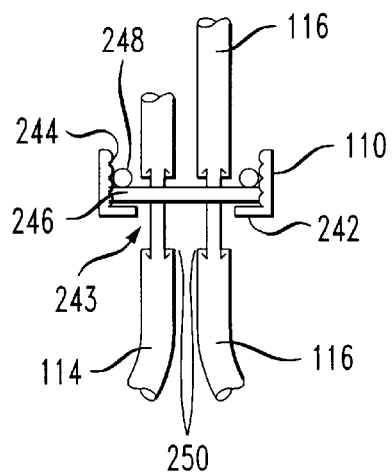
FIG. 2 depicts a side view of the threaded top of a vial, used for engaging the reservoir to the dispenser of FIG. 1.

FIG. 2 depicts an illustrative arrangement by which liquid conduit 114 and gas conduit 116 engage reservoir 108. Stainless plate 246 overlies the lip 242 of lid 110. Lip 242 defines opening 243. The opening provides access for fittings 250, such as Micro-Barb™ fittings available from Beswick Engineering of Greenland, N.H., that extend through plate 246. Tubing, such as TYGON™ tubing available from Norton Performance Plastics, Akron, Ohio, is attached to both ends of both fittings 250. O-ring 244 seals plate 246 to reservoir 108 preventing leakage therefrom.

Thus, as described above, dispensing valve 106 dispenses or aspirates an amount of liquid during its cycle. The dispensed amount, which is usually controlled to a specific volume, is primarily a function of the amount of time that dispensing valve 106 is open, and of the pressure level in liquid conduit 114 or reservoir 108. To a lesser extent, the dispensed amount also depends on fluid properties (e.g., viscosity, etc.).

Various optional features for improving the accuracy the liquid dispensing operation are described below. Such features are described in further detail in applicant's co-pending U.S. patent application Ser. No. 09/395,383, entitled "Article and Method for Flow Control in Liquid Dispensing Devices," which was filed on even date herewith and is incorporated by reference herein.

Dispensers that provide a constant "re-supply" of liquid to replace dispensed fluid, such as illustrative dispenser 100 depicted in FIG. 1, are susceptible to a characteristic error. The error is related to characteristics of the dispensing valve. In particular, the amount of fluid dispensed from such dispensers is proportional to the amount of time that the dispensing valve is open. The behavior of dispensing valves (e.g., valve 106) that are typically used in such dispensers is such that there is a rapid response to an impulse (e.g., voltage) to open, but the closure response tends to be less precise, as a function of the spring used in the valve.

Figure 3:
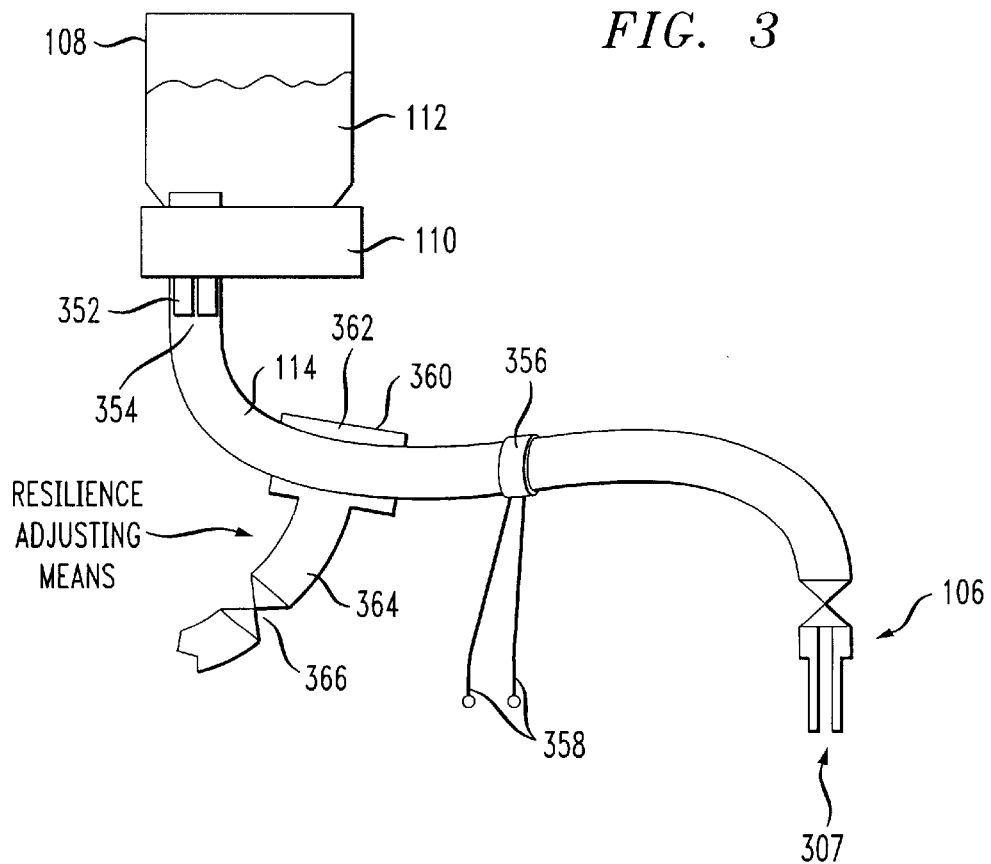
FIG. 3 depicts several flow control features for use in conjuction with the resent invention.

In some embodiments of the present invention, a flow restriction, realized in the illustrative embodiment depicted in FIG. 3 as restriction orifice 352, is disposed in liquid conduit 114. Advantageously, the flow restriction is disposed at the input (i.e., at the interface between reservoir 108 and the liquid conduit 114) of liquid conduit 114. In some embodiments, liquid conduit 114 is elastic, or has a region that is elastic, such that it functions as an accumulator or bladder. Restriction orifice 352 has an outlet orifice 354 that is smaller than opening 307 of dispensing valve 106. As a result, liquid 112 is re-supplied to liquid conduit 114 more slowly than it is dispensed through valve 106. Errors resulting from any delay in valve closure are therefore reduced in magnitude since the flow rate to the valve is reduced by limiting the re-supply rate.

It is advantageous to monitor the pressure in liquid conduit 114 as it falls and rises during respective dispensing and refilling cycles. Such pressure data can be correlated to an amount of liquid dispensed and also provide indications of operational problems (e.g., occlusions in liquid conduit 114).

As such, in some embodiments of the present invention, pressure sensing is provided. Dynamic pressure sensors are advantageously used for such pressure sensing since they are much less expensive (i.e., about an order of magnitude) than static pressure sensors and typically provide sufficient information. At least a portion of liquid conduit 114 must be elastic to use a dynamic pressure sensor.

Thus, in one embodiment, a dynamic pressure sensor 356 is operatively engaged to an elastic region of liquid conduit 114. Leads 358 from sensor 356 connect to appropriate electronics (not shown) for processing sensor data and displaying and/or recording such data. In some embodiments, the present dispenser includes both a restriction orifice and dynamic pressure sensor to improve accuracy.

Over time, the performance characteristics of a fluid dispenser may change. For example, elastic conduit materials may lose resilience over time. Moreover, variations in fluid parameters (e.g., changes in viscosity, etc.) from use-to-use may affect the fluid dynamics within the dispenser and hence the dispensing operation itself. To the extent such a change in elasticity or fluid parameters vary from a baseline condition, an error in the amount of liquid dispensed will occur.

In accordance with the present teachings, in some embodiments, the present dispenser further includes resilience-adjusting means that is operable to adjust the "resilience" or "elasticity" of an elastic region of liquid conduit 114. By appropriately adjusting the resilience-adjusting means, dispenser operation can be maintained at a baseline notwithstanding changed system conditions. Such adjustment is routinely performed via trial and error, wherein the resilience-adjusting means is changed and the dispensed volume is measured. The resilience-adjusting means is adjusted until the proper volume is dispensed. Of course, a user can adjust valve operation and/or pressure to affect changes in the dispensed volume, as well.

In the embodiment depicted in FIG. 3, the resilience-adjusting means comprises an enclosure 360 that defines a pressure-tight chamber 362 surrounding at least a portion of an elastic region of liquid conduit 114, and a pressure-adjustment means. Increasing the pressure within chamber 362 effectively increases the resilience of the enclosed region of liquid conduit 114.

In some embodiments, pressure-adjustment means is implemented by gas supply conduit 364 that delivers gas (e.g., nitrogen, etc.) to chamber 362, and a pressure regulator 366. Additionally, optional vacuum-flow conduit (not shown) for drawing a partial vacuum can be connected to chamber 362.

In further embodiments, the present dispenser includes a restriction orifice, dynamic pressure sensor and resilience-adjusting means for improving dispenser accuracy. In other embodiments, the present dispenser includes various combinations of such flow-control elements.

It is to be understood that the above-described embodiments are merely illustrative of the invention and that many variations may be devised by those skilled in the art without departing from the scope of the invention. It is therefore intended that such variations be included within the scope of the following claims and their equivalents.

I claim:

1. An apparatus comprising:
   a body portion and a head portion;
   a liquid reservoir that is removably engaged to said head portion, wherein said liquid reservoir has a mouth and a bottom, and wherein said mouth is proximal to said head portion;
   a valve capable of passing controllable, micro-liter quantities of a liquid;
   a first conduit that places said liquid reservoir and said valve in fluid communication, wherein said first conduit has a first end and a second end, and wherein said first end of said first conduit protrudes into said liquid reservoir when said liquid reservoir is engaged to said head portion; and
   a second conduit that alternately delivers pressurized gas to said liquid reservoir and places said liquid reservoir under partial vacuum; wherein said second conduit has a first end and a second end, and wherein said first end of said second conduit protrudes into said liquid reservoir when said liquid reservoir is engaged to said head portion.

2. The apparatus of claim 1 further comprising a pressurized gas supply, wherein said pressurized gas supply is in fluid communication with said second end of said second conduit.

3. The apparatus of claim 2 further comprising a mode selector that controllably places said pressurized gas supply in fluid communication with said second end of said second conduit.

4. The apparatus of claim 3 further comprising a suction-flow generator, wherein said mode selector controllably places said suction-flow generator in fluid communication with said second end of said second conduit.

5. The apparatus of claim 1 wherein said first conduit has a flow restriction, and further wherein:
   said flow restriction has an outlet orifice;
   said valve has an opening;
   said outlet orifice is smaller than said opening.

6. The apparatus of claim 1 wherein at least a portion of said first conduit is elastic.

7. The apparatus of claim 5 wherein at least a portion of said first conduit is elastic.

8. The apparatus of claim 6 further comprising a dynamic pressure sensor that senses pressure within said elastic portion of said first conduit.

9. The apparatus of claim 7 further comprising a dynamic pressure sensor that senses pressure within said elastic portion of said first conduit.

10. The apparatus of claim 6 further comprising a resilience-adjusting means that adjusts a resilience of said elastic portion of said first conduit.

11. The apparatus of claim 7 further comprising a resilience-adjusting means that adjusts a resilience of said elastic portion of said first conduit.

12. The apparatus of claim 1 wherein said head portion is removably attached to said body portion.

13. The apparatus of claim 1 further comprising a switch that actuates said valve, wherein said switch is disposed in said body portion.

14. The apparatus of claim 1 wherein said first end of said first conduit is proximal to said mouth of said reservoir, and said first end of said second conduit is proximal to said bottom of said reservoir.

* * * * *